United States Patent [19]

Tognella et al.

[11] Patent Number: 5,446,187
[45] Date of Patent: Aug. 29, 1995

[54] AMINOACYL DERIVATIVES OF GEM-DIPHOSPHONIC ACIDS, A PROCESS FOR THE PREPARATION THEREOF AND PHARMACEUTICAL COMPOSITIONS CONTAINING THEM

[75] Inventors: Sergio Tognella; Valeria Livi; Ernesto Menta; Silvano Spinelli, all of Milan, Italy

[73] Assignee: Boehringer Mannheim Italia S.p.A., Milan, Italy

[21] Appl. No.: 129,098

[22] PCT Filed: Apr. 3, 1992

[86] PCT No.: PCT/EP92/00746
§ 371 Date: Oct. 8, 1993
§ 102(e) Date: Oct. 8, 1993

[87] PCT Pub. No.: WO92/18512
PCT Pub. Date: Oct. 29, 1992

[30] Foreign Application Priority Data

Apr. 12, 1991 [IT] Italy .................. MI91A1016

[51] Int. Cl.$^6$ ............ C07F 9/38; C07F 9/40; A61K 31/66

[52] U.S. Cl. .................. 562/13; 548/957; 558/155; 558/159; 560/38; 560/47; 560/169; 560/172

[58] Field of Search .......... 562/13; 514/107; 548/957; 560/38, 47, 169, 172; 558/155, 159

[56] References Cited

U.S. PATENT DOCUMENTS

| | | | |
|---|---|---|---|
| 4,608,368 | 8/1986 | Blum et al. | 514/107 |
| 4,666,895 | 5/1987 | Bosies et al. | 514/108 |
| 5,019,651 | 5/1991 | Kieczykowski | 562/13 |
| 5,300,671 | 4/1994 | Tognella et al. | 558/159 |

FOREIGN PATENT DOCUMENTS 0197478 10/1986 European Pat. Off. .

OTHER PUBLICATIONS

WO A, 9 105 791 May 2, 1991.

*Primary Examiner*—José G. Dees
*Assistant Examiner*—Barbara S. Frazier
*Attorney, Agent, or Firm*—Nikaido, Marmelstein, Murray & Oram

[57] ABSTRACT

Diphosphonic acids of formula (I) are useful as antitumor agents.

10 Claims, No Drawings

AMINOACYL DERIVATIVES OF GEM-DIPHOSPHONIC ACIDS, A PROCESS FOR THE PREPARATION THEREOF AND PHARMACEUTICAL COMPOSITIONS CONTAINING THEM

This application is a 371 of PCT/EP92/00746, Apr. 3, 1993.

The present invention relates to diphosphonic acid having a marked antitumor activity, to a process for the preparation thereof and to pharmaceutical compositions containing them.

Gem-diphosphonic acids and the salts thereof are known and used in the therapy of osteoporosis and in the treatment of bone resorption (see EP 96.931, EP 252.504, BE 896.453, BE 903.519, DE 3.016.289, DE 3.540.150, DE 2.534.391).

Moreover, diphosphonic acid esters having pesticide activity are disclosed in U.S. Pat. No. 3,906,062. However, no compounds described in the above mentioned patents have been reported to have intrinsic antitumour activity.

DE 3.425.812 discloses 1,1-diphosphonic acid derivatives having a bis[(haloalkyl)amino]phenyl residue as agents useful for the treatment of bone tumors. In fact, beside having the bone tropism characteristic of diphosphonic acids, they also have the typical cytotoxic activity of molecules bearing dialkylating functions.

Metotrexate diphosphonic analogs are described in WO 88/06158 to be useful agents in the treatment of bone tumours.

EP 0197478 describes aminoacyl-derivatives of alkylenediphosphonic acids having therapeutic activity in the treatment of osteoporosis, Paget's disease, Betcherew's disease and tumor mediate bone resorption.

It has now been found that aminoacyl diphosphonic acid derivatives characterized by the presence of a bond which can be physiologically hydrolyzed, connecting the diphosphonic derivative with a dialkylating residue, have, compared with the above cited compounds, advantageous antitumour and antimetastatic properties, which could not be predicted on the basis of their chemical structure and of the presumed bioconversion thereof into the separate components (diphosphonic derivative and alkylating derivative).

The present invention relates to compounds of formula (I)

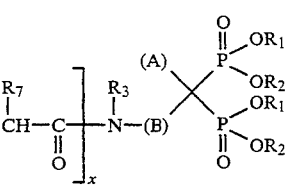

wherein:
R$_1$ and R$_2$, which can be the same or different, are hydrogen or C$_1$-C$_4$ alkyl;
(A) is hydrogen, halogen (chlorine, bromine or iodine), hydroxy, straight or branched C$_1$-C$_{12}$ alkyl;
(B) is a covalent bond, straight or branched C$_1$-C$_8$ alkylene, an alkylene chain containing at least one hetero-atom of formula —[CH(CH$_3$)]$_p$—(CH$_2$)$_{n1}$—X—(CH$_2$)$_n$— or, together with the adjacent nitrogen atom, a group of formula

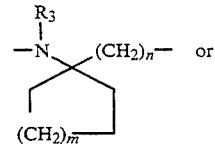

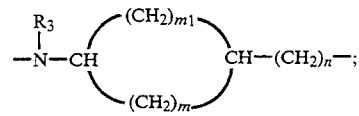

if R$^3$ is absent, heterocyclic rings of formula

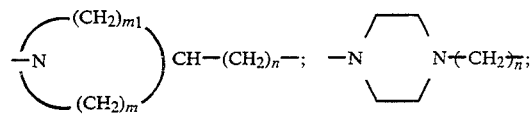

an ortho, meta or para substituted aralkyl of formula

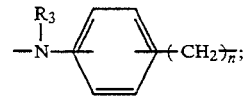

in which
chain or groups X is O, S, N—CH$_3$;
m is zero or the integer 1 or 2;
m$_1$ is the integer 1, 2, 3 or 4;
n and n$_1$ are an integer from 1 to 5;
p is zero or the integer 1;
R$_3$ is hydrogen, straight or branched C$_1$-C$_{10}$ alkyl, C$_3$-C$_6$ cycloalkyl, benzyl, phenyl, or p-methoxybenzyl;
(C) is straight or branched C$_1$-C$_5$ alkylene, phenylene, an aralkyl chain of formula

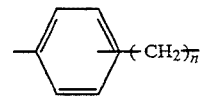

wherein
n is as defined above;

R$_4$ is selected from hydrogen, straight or branched C$_1$-C$_4$ alkyl, or R$_4$ represents a group

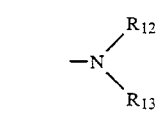

wherein $R_{12}$ and $R_{13}$, which are the same or different, are hydrogen, straight or branched $C_1$–$C_6$ alkyl, phenyl, benzyl, para-methoxybenzyl, or one of $R_{12}$ and $R_{13}$ is as defined above and the other one is a group of formula:

$$R_{14}-\underset{\underset{O}{\|}}{C}-$$

wherein $R_{14}$ is hydrogen, straight or branched $C_1$–$C_4$ alkyl, phenyl, benzyl, para-methoxybenzyl, straight or branched $C_1$–$C_4$ alkoxyl, halo-$C_1$–$C_4$ alkoxyl;

$R_5$ and $R_6$ are haloethyl (2-chloroethyl, 2-bromoethyl, 2-iodoethyl) or $R_5$ and $R_6$, taken together with the nitrogen atom to which they are linked, are a 1-azyridinyl group of formula $$-N\triangleleft;$$

$R_7$, $R_8$, $R_9$ e $R_{10}$, which are the same or different, taken together with the $$-\underset{|}{N}-\underset{|}{CH}-CO-$$

group to which they are linked, are the residue from a D or L amino acid;

$R_{11}$ is hydrogen or straight or branched $C_1$–$C_{12}$ alkyl chain;

x is zero or the integers 1 and 2;

y and z are zero or the integer 1, with the proviso that:

when x, y and z are at the same time zero, (B) is one of the residues of formula $$-N\underset{(CH_2)_{m1}}{\overset{(CH_2)_m}{\diagup}}CH-(CH_2)_n- \quad \text{or} \quad -N\diagup\diagdown N\text{-}(CH_2)_n$$

The present invention also relates to racemates, diastereoisomers and optically pure forms of compounds of general formula I.

The present invention also relates to the pharmaceutically acceptable salts of compounds of general formula (I), for example with inorganic bases, such as salts with alkali metals (such as sodium or potassium) or alkaline-earth metals (such as calcium or magnesium) or ammonium salts; salts with organic bases such as methylamine, ethylamine, propylamine, isopropylamine, butylamine, t-butylamine, dimethylamine, diethylamine, diethanolamine, trimethylamine, triethylamine, piperidine, pyridine, picoline, dicyclohexylamine; organic acid addition salts, such as: formate, acetate, trifluoroacetate, maleate, fumarate, tartrate, methanesulfonate, benzenesulfonate, toluenesulfonate, salts; inorganic acid addition salts, such as hydrochloride, hydrobromide, sulfate, hydrogen sulfate, phosphate salts, or with amino acids, such as aspartate, glutamate or lysine or arginine salts.

$C_1$–$C_4$ Alkyl includes methyl, ethyl, n-propyl, isopropyl, n-butyl, t-butyl, isobutyl or sec-butyl; methyl and ethyl being particularly preferred.

$C_1$–$C_{12}$ Alkyl, besides the meanings precised above for $C_1$–$C_4$ alkyl, can be n-pentyl, n-hexyl, n-decyl and the like; methyl and ethyl being particularly preferred.

A is preferably hydroxy.

The alkylene chain B is preferably —$(CH_2)_n$—, with n comprised from 2 to 5, $$-\underset{\underset{CH_3}{|}}{CH}-(CH_2)_r-$$

with r comprised from 2 to 5, or one of the chains of formula

[cyclopentyl-$(CH_2)_n$— and cyclohexyl-$(CH_2)_n$—]

with n comprised from 1 to 4, or, considered together with the adjacent nitrogen atom, one of the chains of formula

[piperidinyl-$(CH_2)_n$, pyrrolidinyl-$(CH_2)_n$, and piperazinyl-$(CH_2)_n$]

with n comprised from 1 to 3.

$R_1$ and $R_2$ are preferably hydrogen.

$R_3$ is preferably hydrogen or methyl, whereas (C) is preferably

[phenyl-$CH_2$— or phenyl-$(CH_2)_2$—].

When (C) is

[phenyl-$CH_2$—], $R_4$ is preferably a group of formula $$-N\underset{R_{13}}{\overset{R_{12}}{\diagup}}$$

wherein $R_{12}$ and $R_{13}$ are preferably hydrogen or one of them is $R_{14}$—CO—, wherein $R_{14}$ is hydrogen, methyl, tertbutyloxy, trichloromethoxy, trichloroethoxy, benzyloxy, ethoxy.

When (C) is a residue of formula

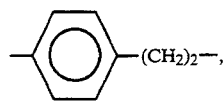

$R_4$ is preferably hydrogen.
$R_5$ and $R_6$ are preferably 2-chloroethyl.
$R_{7D}$, $R_8$, $R_9$ and $R_{10}$, taken together with the

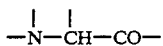

group to which they are linked are preferably the residue from the D or L amino acids glycine, sarcosine, alanine, phenylalanine, valine, leucine, isoleucine, methionine, proline.

$R_{11}$ is preferably hydrogen, methyl, ethyl.

Preferred compounds are those in which: z is 1 and x and y are zero; x and y are different from zero and z is zero; particularly preferred compounds are those in which x is 1 and y and z are zero. Examples of compounds of the invention are:

N-[[4-[bis(2-chloroethyl)amino]-(L)-phenylalanyl]-(L)-alanyl]-4-amino-1-hydroxybutane-1,1-diphosphonic acid;

N-[[4-[bis(2-chloroethyl)amino]-(L)-phenylalanyl]-(D)-alanyl]-4-amino-1-hydroxybutane-1,1-diphosphonic acid;

N-[[4-[bis(2-chloroethyl)amino]-(L)-phenylalanyl]-(L)-alanyl]-5-amino-1-hydroxypentane-1,1-diphosphonic acid;

N-[[4-[bis(2-chloroethyl)amino]-(L)-phenylalanyl]-(D)-alanyl]-5-amino-1-hydroxypentane-1,1-diphosphonic acid;

N-[[4-[bis(2-chloroethyl)amino]-(L)-phenylalanyl]-glycyl]-4-amino-1-hydroxybutane-1,1-diphosphonic acid;

N-[[4-[bis(2-chloroethyl)amino]-(L)-phenylalanyl]-glycyl]-5-amino-1-hydroxypentane-1,1-diphosphonic acid;

N-methyl-N-[[4-[bis(2-chloroethyl)amino]-(L)-phenylalanyl]glycyl]-4-amino-1-hydroxybutane-1,1-diphosphonic acid;

N-[[4-[bis(2-chloroethyl)amino]-(L)-phenylalanyl]-(L)-prolyl]-3-amino-1-hydroxypropane-1,1-diphosphonic acid;

N-[[4-[bis(2-chloroethyl)amino]-(L)-phenylalanyl]-(L)-prolyl]-5-amino-1-hydroxypentane-1,1-diphosphonic acid;

N-[[4-[bis(2-chloroethyl)amino]-(L)-phenylalanyl]-(L)-γ-glutamyl]-5-amino-1-hydroxypentane-1,1-diphosphonic acid;

N-[[4-[bis(2-chloroethyl)amino]-(L)-phenylalanyl]-(L)-γ-glutamyl]-4-amino-1-hydroxybutane-1,1-diphosphonic acid;

3-[4-[[4-[bis(2-chloroethyl)amino]-(L)-phenylalanyl]-(L)-alanyl]piperazin-1-yl]-1-hydroxypropane-1,1-diphosphonic acid;

4-[4-[[4-[bis(2-chloroethyl)amino]-(L)-phenylalanyl]-(L)-alanyl]piperazin-1-yl]-1-hydroxybutane-1,1-diphosphonic acid;

N-[[4-[bis(2-chloroethyl)amino]-(L)-phenylalanyl]-(L)-leucyl]-3-amino-1-hydroxypropane-1,1-diphosphonic acid;

N-[[4-[bis(2-chloroethyl)amino]-(L)-phenylalanyl]sarcosyl]-4-amino-1-hydroxybutane-1,1-diphosphonic acid;

N-[[4-[bis(2-chloroethyl)amino]-(L)-phenylalanyl]-(L)-valyl]-4-amino-1-hydroxybutane-1,1-diphosphonic acid;

N-[[4-[bis(2-chloroethyl)amino]-(L)-phenylalanyl]-glycylglycyl]-5-amino-1-hydroxypentane-1,1-diphosphonic acid;

N-[[4-[bis(2-chloroethyl)amino]-(L)-phenylalanyl]-(L)-alanyl-glycyl]-4-amino-1-hydroxybutane-1,1-diphosphonic acid;

N-[[4-[bis(2-chloroethyl)amino]-(L)-phenylalanyl]-glycylglycylglycyl]-4-amino-1-hydroxybutane-1,1-diphosphonic acid;

N-[[4-[bis(2-chloroethyl)amino]-(L)-phenylalanyl]-(L)-alanyl-(L)-alanyl]-5-amino-1-hydroxypentane-1,1-diphosphonic acid;

N-[[4-[4-[bis(2-chloroethyl)amino]phenyl]butyroyl]-(L)-alanyl]-4-amino-1-hydroxybutane-1,1-diphosphonic acid;

N-[[4-[4-[bis(2-chloroethyl)amino]phenyl]butyroyl]-(D)-alanyl]-4-amino-1-hydroxybutane-1,1-diphosphonic acid;

N-[[4-[4-[bis(2-chloroethyl)amino]phenyl]butyroyl]-(L)-alanyl]-5-amino-1-hydroxypentane-1,1-diphosphonic acid;

N-[[4-[4-[bis(2-chloroethyl)amino]phenyl]butyroyl]-(D)-alanyl]-5-amino-1-hydroxypentane-1,1-diphosphonic acid;

N-[[4-[4-[bis(2-chloroethyl)amino]phenyl]butyroyl]-glycyl]-4-amino-1-hydroxybutane-1,1-diphosphonic acid;

N-[[4-[4-[bis(2-chloroethyl)amino]phenyl]butyroyl]-glycyl]-5-amino-1-hydroxypentane-1,1-diphosphonic acid;

N-methyl-N-[[4-[4-[bis(2-chloroethyl)amino]phenyl]butyroyl]glycyl]-4-amino-1-hydroxybutane-1,1-diphosphonic acid;

N-[[4-[4-[bis(2-chloroethyl)amino]phenyl]butyroyl]-(L)-prolyl]-3-amino-1-hydroxypropane-1,1-diphosphonic acid;

N-[[4-[4-[bis(2-chloroethyl)amino]phenyl]butyroyl]-(L)-γ-glutamyl]-5-amino-1-hydroxypentane-1,1-diphosphonic acid;

N-[[4-[4-[bis(2-chloroethyl)amino]phenyl]butyroyl]-(L)-γ-glutamyl]-4-amino-1-hydroxybutane-1,1-diphosphonic acid;

N-[[4-[4-[bis(2-chloroethyl)amino]phenyl]butyroyl]-(L)-propyl]-5-amino-1-hydroxypentane-1,1-diphosphonic acid;

3-[4-[[4-[4-[bis(2-chloroethyl)amino]phenyl]butyroyl]-(L)-alanyl]-piperazin-1-yl]-1-hydroxypropane-1,1-diphosphonic acid;

4-[4-[[4-[4-[bis(2-chloroethyl)amino]phenyl]butyroyl]-(L)-alanyl]-piperazin-1-yl]-1-hydroxybutane-1,1-diphosphonic acid;

N-[[4-[4-[bis(2-chloroethyl)amino]phenyl]butyroyl]-(L)-valyl]-5-amino-1-hydroxypentane-1,1-diphosphonic acid;

N-[[4-[4-[bis(2-chloroethyl)amino]phenyl]butyroyl]-glycylglycyl]-5-amino-1-hydroxypentane-1,1-diphosphonic acid;

N-[[4-[4-[bis(2-chloroethyl)amino]phenyl]butyroyl]-(L)-alanyl-glycyl]-4-amino-1-hydroxybutane-1,1-diphosphonic acid;

N-[[4-[4-[bis(2-chloroethyl)amino]phenyl]butyroyl]-(L)-alanyl-(L)-alanyl-(L)-alanyl]-5-amino-1-hydroxypentane-1,1-diphosphonic acid;
3-[4-[4-[bis(2-chloroethyl)amino]-(L)-phenylalanyl]-piperazin-1-yl]-1-hydroxypropane-1,1-diphosphonic acid;
4-[4-[4-[bis(2-chloroethyl)amino]-(L)-phenylalanyl]-piperazin-1-yl]-1-hydroxybutane-1,1-diphosphonic acid;
N-[4-[bis(2-chloroethyl)amino]-(L)-phenylalanyl]-3-(pirrolidin-2-yl)-1-hydroxypropane-1,1-diphosphonic acid;
N-[4-[bis(2-chloroethyl)amino]-(L)-phenylalanyl]-3-(piperidin-4-yl)-1-hydroxypropane-1,1-diphosphonic acid;
N-[4-[bis(2-chloroethyl)amino]-(L)-phenylalanyl]-3-(piperidin-2-yl)-1-hydroxypropane-1,1-diphosphonic acid;
N-[4-[bis(2-chloroethyl)amino]-(L)-phenylalanyl]-2-(piperidin-2-yl)-1-hydroxyethane-1,1-diphosphonic acid;
N-[[4-[4-[bis(2-chloroethyl)amino]phenyl]butyroyloxy]acetyl]-4-amino-1-hydroxybutane-1,1-diphosphonic acid;
N-[[4-[4-[bis(2-chloroethyl)amino]phenyl]butyroyloxy]acetyl]-3-(piperidin-2-yl)-1-hydroxypropane-1,1-diphosphonic acid;
N-[[4-[4-[bis(2-chloroethyl)amino]phenyl]butyroyloxy]acetyl]-5-amino-1-hydroxypentane-1,1-diphosphonic acid;
N-[[4-[bis(2-chloroethyl)amino]-(L)-phenylalanyloxy]acetyl]-4-amino-1-hydroxybutane-1,1-diphosphonic acid;
N-[[4-[bis(2-chloroethyl)amino]-(L)-phenylalanyloxy]acetyl]-3-(pirrolidin-2-yl)-1-hydroxypropane-1,1-diphosphonic acid.

The compounds of the present invention are prepared by reacting a compound of formula (II)

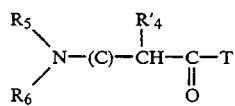

wherein $R_5$, $R_6$ and (C) have the above mentioned meanings and $R'_4$ is the same as $R_4$ or it is a group which can be converted into $R_4$ by removing any protecting groups, T is hydroxy or a carboxy-activating group, with a compound of formula (III)

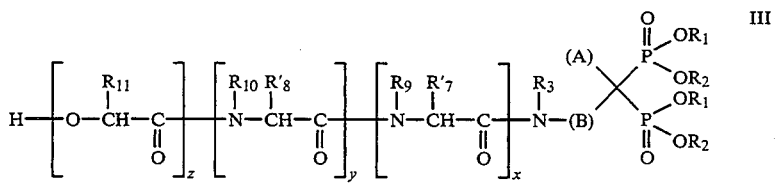

wherein $R_1$, $R_2$, $R_3$, $R_9$, $R_{10}$, $R_{11}$, (A), (B), x, y and z have the above mentioned meanings and $R'_7$ and $R'_8$ have the same meanings as $R_7$ and $R_8$ or they can be converted into $R_7$ and $R_8$ by removing the amino-, hydroxy-, thio-and carboxy-protecting groups which can optionally be present, to give a compound of formula (Ia):

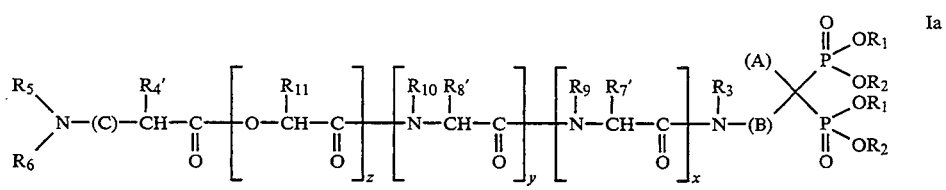

wherein $R_1$, $R_2$, $R_3$, $R'_4$, $R_5$, $R_6$, $R_7'$, $R_8'$, $R_9$, $R_{10}$, $R_{11}$, (A), (B), (C), x, y and z have the above mentioned meanings, which compound in its turn can be transformed into a compound of formula (I) by means of known reactions for the selective removal of protecting groups, alkylation or acylation of amino groups and the like.

When, in the reaction of compounds of formula (II) with compounds of formula (III), compounds of formula (II) are used in form of carboxylic acids (T=OH), the reaction is usually carried out in the presence of a condensing agent, such as N,N'-dicyclohexylcarbodiimide, N-cyclohexyl-N'-morpholinoethyl-carbodiimide, N-ethyl-N'-(3-dimethylamino)-propyl-carbodiimide, N,N'-carbonyl-bis-(imidazole), phosphorous oxychloride, phosphorous trichloride, thionyl chloride, oxalyl chloride, ethyl chloroformate, isobutyl chloroformate, morpholinoethyl isocyanide and the like. Examples of carboxy-activating groups are acyl halides, symmetric or mixed anhydrides (such as with methanesulfonic, acetic, isobutyric, pivalic, trichloroacetic acids); reactive amides (for example with imidazole, 1,2,4-triazole); azide; reactive esters (such as paranitrophenyl ester, methoxymethyl ester, 2,4-dinitrophenyl ester, pentachlorophenyl ester, hydroxysuccinimide ester, 1-hydroxy-2-(1H)-pyridone ester, 1-hydroxybenzotriazole ester) and the like. The reaction can be performed in the presence of an inorganic base, such as an alkali carbonate or bicarbonate, an alkali or alkaline-earth hydroxide or an organic base such as triethylamine, tributylamine, pyridine, 4-dimethylamino-pyridine, N-alkylmorpholine, N,N-dialkyl-aniline and the like.

The reaction can be effected at a temperature ranging from −40° C. to the reflux temperature of the solvent preferably using a slight molar excess of compound (II) compared to (III) in a solvent such as water, N,N-dimethylformamide or mixtures thereof.

The reaction temperature preferably ranges from −10° C. to room temperature and, in this case, the reaction time ranges from 1 to 48 hours, but generally the reaction is complete within a time from 2 to 12 hours.

Compounds of general formula (II) are known compounds, which are commercially available and/or can be prepared by known methods to those skilled in the art, such as those described in: J. Med. Chem. 24, 1304, (1981); CA 51: 8066(d), (1957); BE 905,974; CA 104: 141897 (1986); J. Med. Chem. 7, 468, (1964); J. Med. Chem. 6, 85, (1963); Cancer Chem. Rep. 50, 685, (1966); J. Med. Chem. 21, 16, (1977); J. Org. Chem. 26, 1554, (1961); J. Org. Chem. 26, 1674, (1961); CA 64; 10267 g, (1966); J. Chem. Soc., 2994, (1960); Biochem. Pharmacol. 11, 847, (1962); Biochem. Pharmacol. 12, 833, (1963); CA 73: 131293c, (1970); Biochem. Pharmacol. 5, 192, (1960); Int. J. Pept. Protein Res., 36, 308, (1990).

Compounds of formula (III) wherein z is zero and x and y are as defined above are also known or they can be prepared according to known methods; see, for instance, EP 96931, EP 252504, BE 903519, DE 3016289, EP 224751, DE 2534391, EP 197478, DE 3512536 e DE 3623397.

Compounds of formula (III) wherein z is 1 are not known, but they can be prepared by reacting a compound of formula (IV):

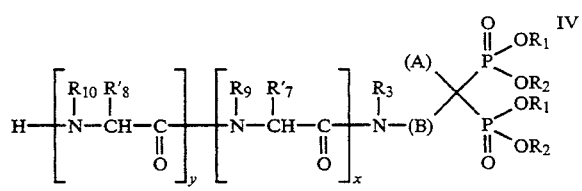

wherein $R_1$, $R_2$, $R_3$, $R'_7$, $R'_8$, $R_9$, $R_{10}$, (A), (B), x and y have the above mentioned meanings, with a compound of formula (V):

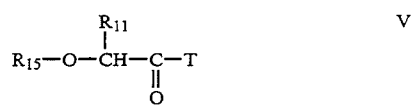

wherein $R_{11}$ and T have the above mentioned meanings and $R_{15}$ is a hydroxy-protecting group, to give a compound of formula (VI):

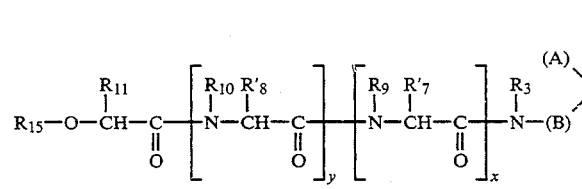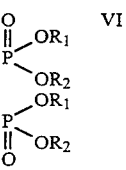

which, by removing the protective group $R_{15}$, gives a compound of formula (III) wherein z is 1.

If desired, compounds of general formula (I) wherein $R_1$ and $R_2$ are different from hydrogen, can optionally be transformed into the corresponding gem-diphosphonic acids by treatment with a molar excess of trialkylsilyl-chloride, -iodide or -bromide in a halogenated solvent such as dichloromethane, 1,2-dichloroethane, 1,1,2-trichloroethane and the like. Trimethylsilyl iodide is preferably used.

The reaction times ranges from a few minutes to 72 hours; the reaction temperatures range from 0° C. to the solvent's reflux temperature; preferred reaction conditions are those according to J. Org. Chem: 28, 2975-78, (1963).

The removal of the secondary- or primary-amine protecting groups optionally present in the compounds of general formula (I) can be carried out according to well-known techniques, particularly those used in peptide synthesis.

The compounds of the invention have high cytotoxic activity against tumour cells, as it can be evidenced by means of "in vitro" tests carried out, for instance, according to the procedure described by M. P. Hacker, Cancer Res. 45, 4748, (1985). The $ID_{50}$ (i.e. the compound dose which can inhibit by 50% the growth of "in vitro" cultured murine and human tumour cells of both solid and hematic tumors) of the compounds of the invention were found to be comprised from 0.1 to 5 µg/ml of culture medium. Under these test conditions, the compounds of the invention: N-[[4-[bis(2-chloroethyl)amino]-(L)-phenylalanyl]-(L)-alanyl]-4-amino-1-hydroxybutane-1,1-diphosphonic acid monohydrochloride and N-[[4-[4-[bis(2-chloroethyl)amino]phenyl]-butyroyl]-(L)-alanyl]-4-amino-1-hydroxybutane-1,1-diphosphonic acid disodium salt have an $ID_{50}$ of 0.1 γ/ml and 0.5 γ/ml, respectively, against murine leukemia L1210.

The compounds of the invention are characterized by a low acute toxicity and are well tolerated by the animals.

The compounds of the invention have a high therapeutical index, in light of the low toxicity and the effective antitumor activity thereof. Moreover, the high water-solubility of the compounds of the present invention allows the easy preparation of parenteral and oral pharmaceutical forms.

The compounds of formula (I), when administered to humans and animals affected with tumours which can be treated with alkylating agents, at doses ranging from 1 mg/m² to 1.2 g/m² body area, can induce the regression of the above mentioned tumoral forms.

The effective dosage for the compounds of the invention can be determined by the expert clinicians according to conventional methods. The relationship between the dosages used for various animal species and those for humans (on the basis of mg/m² body area) is described by Freireich, E. J., et al., Quantitative Comparison of Toxicity of Anticancer Agents in Mouse, Rat, Hamster, Dog, Monkey and Man, Cancer Chemother. Rep., 50, n. 4, 219–244, May 1966.

The tumours which can be treated with the compounds of the present invention are those susceptible to therapy with alkylating agents. Particularly, multiple myeloma, osteosarcoma, bone metastatis and breast, ovarian and testis carcinomas can be advantageously treated.

Moreover, the compounds of the invention can advantageously be used in the therapy of other solid and liquid tumors, such as lymphomas and leukemias.

The compounds of the invention can be administered by the parenteral route (intravenously, intramuscularly, intraarterially, intraperitoneally) in form of sterile aqueous solutions or sterile powders for the extemporary preparation of solutions, oily preparations for the intramuscular or intraperitoneal administrations.

The compounds of the invention can also be administered by the oral route: in this instance, useful pharmaceutical formulations can be syrups or similar liquid formulations, as well as solid formulations, such as tablets, capsules and the like.

The following Examples further illustrate the invention.

EXAMPLE 1 a) A solution of di(tert-butyl)dicarbonate (900 mg) in tetrahydrofuran (THF; 8 ml) is quickly added to a solution of 4-[bis(2-chloroethyl)amino)]-(L)-phenylalanine (600 mg) in THF (20 ml) and 1N NaOH (2 ml). The resulting mixture is stirred at room temperature for 2 hours, adjusting pH to about 9 by repeated additions of 1N NaOH. After that, solvent is distilled off under vacuum and the residue is partitioned between water (6 ml) and ethyl ether (10 ml).

The organic phase is discarded and the aqueous one is acidified with HCl and repeatedly extracted with ethyl ether. The combined organic extracts are dried over sodium sulfate and concentrated to dryness under vacuum, to obtain a white foamy residue of N'-(tert-butoxycarbonyl)-4-[bis(2-chloroethyl)amino]-(L)-phenylalanine (mg 580).

NMR (CDCl$_3$, TMS) $\delta$=1,4 (s, 9H); 3,1 (m, 2H); 3,65 (m 8H); 4,55 (m, 1H); 4,99 (d, 1H); 6,62 (d, 2H); 7,12 (d, 2H); 8,1 (s, 1H).

b) A stirred solution of the compound obtained in a) (580 mg) in anhydrous THF (10 ml) is added with N-hydroxysuccinimide (346 mg) and morpholinoethyl isocyanide (0.266 ml). The mixture is stirred for one hour at room temperature, then concentrated to dryness under vacuum. The resulting residue is taken up into 2N HCl (10 ml) and repeatedly extracted with ethyl acetate (3×10 ml). The organic phases are combined, washed with 5% aqueous NaHCO$_3$, with water (10 ml) and dried over sodium sulfate. Solvent is evaporated off under vacuum, to obtain an oily residue which is crystallized from an ethyl ether/isopropyl ether mixture, to give 520 mg of N'-(tert-butoxycarbonyl)-4-[bis(2-chloroethyl)amino]-(L)-phenylalanine hydroxysuccinimide ester (melting point 140°–143° C.); [$\alpha$]$_D$=+3,5 (c=2 chloroform) NMR (TMS, CDCl$_3$) $\delta$=1,45 (s, 9H); 2,85 (s, 4H); 3,15 (m, 2H); 3,69 (m, 8H); 4,9 (m, 1H); 6,61 (d, 2H); 7,15 (d, 2H).

c) A solution of the ester obtained in b) (203 mg) in dimethylformammide (DMF; 1 ml) is slowly dropped into a solution of N-[(L)-alanyl]-4-amino-1-hydroxybutane-1,1-diphosphonic acid disodium salt (100 mg) in a mixture of water (4 ml) and DMF (3 ml) adjusted to pH 10.5 by addition of 1N NaOH. During the dropping of the hydroxysuccinimide ester the pH is maintained between 9–10 by repeated additions of 1N NaOH.

At the end of the addition, the pH is brought to 5–5.4 by 2N HCl and the resulting mixture is diluted with methanol (50 ml) and refrigerated (5 minutes); a precipitate separates which is recovered by filtration to yield 120 mg of N-{[N'-(tert-butoxycarbonyl)-4-[bis (2-chloroethyl)amino]-(L)-phenylalanyl]-(L)-alanyl}-4-amino-1-hydroxybutane-1,1-diphosphonic acid disodium salt m.p.>260° C. [$\alpha$]$_D$=4 (c=2 in water).

$^1$H-NMR (TMS, D$_2$O): 1,35 (m, 12H); 1,85 (m, 4H); 2,9 (m, 2H); 3,2 (m, 2H); 3,75 (s, 8H); 4,3 (m, 2H); 6,85 (d, 2H); 7,15 (d, 2H) HPLC: Partisphere C$_{18}$150×4,6 mm; sodium heptanesulfonate 0,025M in water/acetonitrile/dioxane 70:20:10, pH 2,5 with H$_3$PO$_4$; flow 0,8 ml/min; $\lambda$=255 nm Retention time 12,86'.

EXAMPLE 2

Following the procedure described in Example 1, by reacting N'-(tert-butoxycarbonyl)-4-[bis(2-chloroethyl)amino]-(L)-phenylalanine hydroxysuccinimide ester with the appropriate N-(aminoacyl)-aminoalkyl-1-hydroxy-1,1-diphosphonic acids, the disodium salts of the following compounds are obtained:

N-{N'-(tert-butoxycarbonyl)-4-[bis(2-chloroethyl)amino]-(L)-phenylalanyl-(D)-alanyl}-4-amino-1-hydroxybutane-1,1-diphosphonic acid;

N-{N'-(tert-butoxycarbonyl)-4-[bis(2-chloroethyl)amino]-(L)-phenylalanyl-(L)-alanyl}-5-amino-1-hydroxypentane-1,1-diphosphonic acid;

N-{N'-(tert-butoxycarbonyl)-4-[bis(2-chloroethyl)amino]-(L)-phenylalanyl-(D)-alanyl}-5-amino-1-hydroxypentane-1,1-diphosphonic acid;

N-{N'-(tert-butoxycarbonyl)-4-[bis(2-chloroethyl)amino]-(L)-phenylalanyl-glycyl}-4-amino-1-hydroxybutane-1,1-diphosphonic acid;

N-{N'-(tert-butoxycarbonyl)-4-[bis(2-chloroethyl)amino]-(L)-phenylalanyl-glycyl}-5-amino-1-hydroxypentane-1,1-diphosphonic acid;

N-methyl-N-{N'-(tert-butoxycarbonyl)-4-[bis(2-chloroethyl)amino]-(L)-phenylalanyl-glycyl}-4-amino-1-hydroxybutane-1,1-diphosphonic acid;

N-{N'-(tert-butoxycarbonyl)-4-[bis(2-chloroethyl)amino]-(L)-phenylalanyl-(L)-prolyl}-3-amino-1-hydroxypropane-1,1-diphosphonic acid;

N-{N'-(tert-butoxycarbonyl)-4-[bis(2-chloroethyl)amino]-(L)-phenylalanyl-(L)-prolyl}-5-amino-1-hydroxypentane-1,1-diphosphonic acid;

3-{4-{N'-tert-butoxycarbonyl)-4-[bis(2-chloroethyl)amino]-(L)-phenylalanyl-(L)-alanyl}-piperazin-1-yl}-1-hydroxypropane-1,1-diphosphonic acid;

4-{4-{N'-(tert-butoxycarbonyl)-4-[bis(2-chloroethyl)amino]-(L)-phenylalanyl-(L)-alanyl}-piperazin-1-yl}-1-hydroxybutane-1,1-diphosphonic acid;

N-{N'-(tert-butoxycarbonyl)-4-[bis(2-chloroethyl)amino]-(L)-phenylalanylglycylglycyl}-5-amino-1-hydroxypentane-1,1-diphosphonic acid;

N-{N'-(tert-butoxycarbonyl)-4-[bis(2-chloroethyl)amino]-(L)-phenylalanylglycylglycyl}-4-amino-1-hydroxybutane-1,1-diphosphonic acid;

N-{N'-(tert-butoxycarbonyl)-4-[bis(2-chloroethyl)amino]-(L)-phenylalanyl-(L)-alanylglycyl}-4-amino-1-hydroxybutane-1,1-diphosphonic acid;

N-{N'-(tert-butoxycarbonyl)-4-[bis(2-chloroethyl)amino]-(L)-phenylalanylglycylglycyglycyl}-4-amino-1-hydroxybutane-1,1-diphosphonic acid.

EXAMPLE 3

A solution of N-{N'-(tert-butoxycarbonyl)-4-[bis(2-chloroethyl)amino]-(L)-phenylalanyl-(L)-alanyl}-4-amino-1-hydroxybutane-1,1-diphosphonic acid disodium salt (50 mg) in methanol (1 ml) and 6.9M HCl in ethanol (0.1 ml) is stirred at room temperature for 20 hours, then the reaction mixture is concentrated to small volume and the separated sodium chloride is filtered off. By diluting the filtrate with ethyl ether (10 ml), N-{[4-[bis(2-chloroethylamino)]-(L)-phenylalanyl]-(L)-alanyl}-4-amino-1-hydroxybutane-1,1-diphosphonic acid monohydrochloride precipitates (35 mg).

m.p.=190° C. (decomp.) [α]$_D$=+4,8 (c=2 in methanol) $^1$H-NMR (TMS, HCl 0.1N in D$_2$O): δ=1,3 (d, 3H); 1,75–2,1 (m, 4H); 3,25 (m, 4H); 3,62 (t, 4H); 4,15 (t, 4H); 4,25 (t, 2H); 7,55 (q, 4H) HPCL: Partisphere C$_{18}$, 150×4,6 mm; sodium heptanesulfonate 0,025M in water/acetonitrile/dioxane 70:20:10, pH~2,5 with H$_3$PO$_4$; flow 0,8 ml/min; λ=255 nm Retention time: 4,66'

EXAMPLE 4

Following the procedure described in Example 3, by reacting the disodium salts of the acids described in Example 2, the monohydrochloride salts of the following acids are obtained:

N-{4-[bis(2-chloroethyl)amino]-(L)-phenylalanyl-(D)-alanyl}-4-amino-1-hydroxypentane-1,1-diphosphonic acid;
N-{4-[bis(2-chloroethyl)amino]-(L)-phenylalanyl-(L)-alanyl}-5-amino-1-hydroxypentane-1,1-diphosphonic acid;
N-{4-[bis(2-chloroethyl)amino]-(L)-phenylalanyl-(D)-alanyl}-5-amino-1-hydroxypentane-1,1-diphosphonic acid (trisodium salt);
N-{4-[bis(2-chloroethyl)amino]-(L)-phenylalanyl-glycyl}-4-amino-1-hydroxybutane-1,1-diphosphonic acid;
N-{4-[bis(2-chloroethyl)amino]-(L)-phenylalanyl-glycyl}-5-amino-1-hydroxypentane-1,1-diphosphonic acid;
N-methyl-N-{4-[bis(2-chloroethyl)amino]-(L)-phenylalanyl-glycyl}-4-amino-1-hydroxybutane-1,1-diphosphonic acid;
N-{4-[bis(2-chloroethyl)amino]-(L)-phenylalanyl-(L)-prolyl}-3-amino-1-hydroxypropane-1,1-diphosphonic acid;
N-{4-[bis(2-chloroethyl)amino]-(L)-phenylalanyl-(L)-prolyl}-5-amino-1-hydroxypentane-1,1-diphosphonic acid;
3-{4-[bis(2-chloroethyl)amino]-(L)-phenylalanyl-(L)-alanyl}-piperazin-1-yl}-1-hydroxypropane-1,1-diphosphonic acid;
4-{4-{4-[bis(2-chloroethyl)amino]-(L)-phenylalanyl-(L)-alanyl}-piperazin-1-yl}-1-hydroxybutane-1,1-diphosphonic acid;
N-{4-[bis(2-chloroethyl(amino)]-(L)-phenylalanyl-glycylglycyl}-5-amino-1-hydroxypentane-1,1-diphosphonic acid;
N-{4-[bis(2-chloroethyl)amino]-(L)-phenylalanyl-glycylglycyl}-4-amino-1-hydroxybutane-1,1-diphosphonic acid;
N-{4-[bis(2-chloroethyl)amino]-(L)-phenylalanyl-(L)-alanylglycyl}-4-amino-1-hydroxybutane-1,1-diphosphonic acid;
N-{4-[bis(2-chloroethyl)amino]-(L)-phenylalanyl-glycylglycylglycyl}-4-amino-1-hydroxybutane-1,1-diphosphonic acid.

EXAMPLE 5

Following the procedure described in Example 1, step b), by reacting 4-[4-[bis(2-chloroethyl)amino]-phenyl]butyric acid (1.5 g) with N-hydroxysuccinimide (1.2 g) and N-morpholinoethylisocyanide (0.9 ml), 4-[4-[bis(2-chloroethyl)amino]phenyl]butyric acid N-hydroxysuccinimide ester is obtained (1.88 g), m.p. 80°–82° C.

According to the procedure described in Example 1, step c), the above hydroxysuccinimide ester (830 mg) is reacted with N-[(L)-alanyl]-4-amino-1-hydroxybutane-1,1-diphosphonic acid disodium salt (500 mg), to give N-{4-[4-[bis(2-chloroethyl)amino]phenyl]butyroyl-(L)-alanyl}-4-amino-1-hydroxybutane-1,1-diphosphonic acid disodium salt (820 mg), m.p.>260° C.

$^1$H-NMR (D$_2$O, TMS): δ=1.35 (d, 3H); 1.9 (m, 6H); 2.27 (t, 3H); 2.56 (t, 2H); 3.22 (t, 2H); 3.75 (s, 8H); 4.15 (q, 1H); 6.89 (d, 2H); 7.15 (d, 2H).

EXAMPLE 6

Following the procedure described in Example 5, by reacting 4-[4-[bis(2-chloroethyl)amino]phenyl]butyric acid hydroxysuccinimide ester with the appropriate N-(aminoacyl)-aminoalkyl-1-hydroxy-1,1-diphosphonic acids of disodium salts thereof, the disodium salts of the following compounds are obtained:

N-{[4-[4-[bis(2-chloroethyl)amino]phenyl]butyroyl]-(D)-alanyl}-4-amino-1-hydroxybutane-1,1-diphosphonic acid;
N-{[4-[4-[bis(2-chloroethyl)amino]phenyl]butyroyl]-(L)-alanyl}-5-amino-1-hydroxypentane-1,1-diphosphonic acid;
N-{[4-[4-[bis(2-chloroethyl)amino]phenyl]butyroyl]-(D)-alanyl}-5-amino-1-hydroxypentane-1,1-diphosphonic acid;
N-{[4-[4-[bis(2-chloroethyl)amino]phenyl]butyroyl]-glycyl}-4-amino-1-hydroxybutane-1,1-diphosphonic acid;
N-{[4-[4-[bis(2-chloroethyl)amino]phenyl]butyroyl]-glycyl}-5-amino-1-hydroxypentane-1,1-diphosphonic acid;
N-methyl-N-{[4-[4-[bis(2-chloroethyl)amino]phenyl]butyroyl]glycyl}-4-amino-1-hydroxybutane-1,1-diphosphonic acid;
N-{[4-[4-[bis(2-chloroethyl)amino]phenyl]butyroyl]-(L)-prolyl}-3-amino-1-hydroxypropane-1,1-diphosphonic acid;
N-{[4-[4-[bis(2-chloroethyl)amino]phenyl]butyroyl]-(L)-prolyl}-5-amino-1-hydroxypentane-1,1-diphosphonic acid;
3-{{4-[4-[4-[bis(2-chloroethyl)amino]phenyl]butyroyl]-(L)-alanyl}piperazin-1-yl}-1-hydroxypropane-1,1-diphosphonic acid;
4-{{4-[4-[4-[bis(2-chloroethyl)amino]phenyl]butyroyl]-(L)-alanyl}piperazin-1-yl}-1-hydroxybutane-1,1-diphosphonic acid;
N-{[4-[4-[bis(2-chloroethyl)amino]phenyl]butyroyl]-glycylglycyl}-5-amino-1-hydroxypentane-1,1-diphosphonic acid;
N-{[4-[4-[bis(2-chloroethyl)amino]phenyl]butyroyl]-glycylglycyl}-4-amino-1-hydroxybutane-1,1diphosphonic acid;
N-{[4-[4-[bis(2-chloroethyl)amino]phenyl]butyroyl]-(L)-alanylglycyl}-4-amino-1-hydroxybutane-1,1-diphosphonic acid;
N-{[4-[4-[bis(2-chloroethyl)amino]phenyl]butyroyl]-glycylglycylglycyl}-4-amino-1-hydroxybutane-1,1-diphosphonic acid.

EXAMPLE 7

A solution of 4-[bis(2-chloroethyl)amino]-(L)-phenylalanine (150 mg) in formic acid (1.82 ml) and acetic anhydride (0.64 ml) is stirred at room temperature for 3 hours. The reaction mixture is concentrated under reduced pressure and partitioned between water (3 ml) and ethyl acetate (2×50 ml). The organic phase is dried over sodium sulfate and solvent is evaporated off under vacuum to give N-formyl-4-[bis(2-chloroethyl)amino]-(L)-phenylalanine (160 mg) as a yellow foam, $[\alpha]_D = +67°$ C. (c=2 ethanol)

$^1$H-NMR (CDCl$_3$, TMS): $\delta$=2,9÷3,1 (m, 2H); 3,6 (m, 8H); 4,68÷4,79 (m, 1H); 6,5 (d, 2H+1H); 6,69 (d, 2H); 8,1 (s, 1H).

Following the procedure described in Example 1, steps b) and c), this compound is converted into the hydroxysuccinimide ester thereof (50 mg), which is reacted with N-[(L)-alanyl]-4-amino-1-hydroxybutane-1,1-diphosphonic acid disodium salt (30 mg) to give N-{[N'-formyl-4-[bis(2-chloroethyl)amino]-(L)-phenylalanyl]-(L)-alanyl}-4-amino-1-hydroxybutane-1,1-diphosphonic acid disodium salt (55 mg).

EXAMPLE 8

Following the procedure described in Example 1, step c), by reaction of N-formyl-4-[bis(2-chloroethyl)amino]-(L)-phenylalanine hydroxysuccinimide ester with the appropriate N-(aminoacyl)-aminoalkyl-1-hydroxy-1,1-diphosphonic acids or disodium salts thereof, the disodium salts of the following compounds are obtained:

N-{N'-formyl-4-[bis(2-chloroethyl)amino]-(L)-phenylalanyl -(D)-alanyl}-4-amino-1-hydroxybutane-1,1-diphosphonic acid;

N-{N'-formyl-4-[bis(2-chloroethyl)amino]-(L)-phenylalanyl -(L)-alanyl}-5-amino-1-hydroxypentane-1,1-diphosphonic acid;

N-{N'-formyl-4-[bis(2-chloroethyl)amino]-(L)-phenylalanyl -(D)-alanyl}-5-amino-1-hydroxypentane-1,1-diphosphonic acid;

N-{N'-formyl-4-[bis(2-chloroethyl)amino]-(L)-phenylalanyl -glycyl}-4-amino-1-hydroxybutane-1,1-diphosphonic acid;

N-{N'-formyl-4-[bis(2-chloroethyl)amino]-(L)-phenylalanyl -glycyl}-5-amino-1-hydroxypentane-1,1-diphosphonic acid;

N-methyl-N-{N'-formyl-4-[bis(2-chloroethyl)amino]-(L)-phenylalanyl -glycyl}-4-amino-1-hydroxybutane-1,1-diphosphonic acid;

N-{N'-formyl-4-[bis(2-chloroethyl)amino]-(L)-phenylalanyl -(L)-prolyl}-3-amino-1-hydroxypropane-1,1-diphosphonic acid;

N-{N'-formyl-4-[bis(2-chloroethyl)amino]-(L)-phenylalanyl -(L)-prolyl}-5-amino-1-hydroxypentane-1,1-diphosphonic acid;

3-{4-{N'-formyl-4-[bis(2-chloroethyl)amino]-(L)-phenylalanyl -(L)-alanyl}-piperazin-1-yl}-1-hydroxypropane-1,1-diphosphonic acid;

4-{4-{N'-formyl-4-[bis(2-chloroethyl)amino]-(L)-phenylalanyl -(L)-alanyl}-piperazin-1-yl}-1-hydroxybutane-1,1- diphosphonic acid;

N-{N'-formyl-4-[bis(2-chloroethyl)amino]-(L)-phenylalanylglycylglycyl}-5-amino-1-hydroxypentane-1,1-diphosphonic acid;

N-{N'-formyl-4-[bis(2-chloroethyl)amino]-(L)-phenylalanylglycylglycyl}-4-amino-1-hydroxybutane-1,1-diphosphonic acid;

N-{N'-formyl-4-[bis(2-chloroethyl)amino]-(L)-phenylalanyl-(L)-alanylglycyl}-4-amino-1-hydroxybutane-1,1-diphosphonic acid;

N-{N'-formyl-4-[bis(2-chloroethyl)amino]-(L)-phenylalanylglycylglycylglycyl}-4-amino-1-hydroxybutane-1,1-diphosphonic acid.

EXAMPLE 9

Following the procedure described in Example 1, steps a) and b), $N^6,N^6$-bis(2-chloroethyl)-(DL)-lysine (J. Med. Chem. 7, 468, (1964)) is transformed into $N^2$-(tert-butoxycarbonyl)-$N^6,N^6$-bis(2-chloroethyl)-(DL)-lysine hydroxysuccinimide ester which, according to the procedure described in Example 1, step c), is reacted with N-[(L)-alanyl]-4-amino-1-hydroxybutane-1,1-diphosphonic acid disodium salt to give N-{[$N^2$-(tert-butoxycarbonyl)-$N^6$, $N^6$-bis(2-chloroethyl)-(DL)-lysinyl-(L)-alanyl]}-4-amino-1-hydroxybutane-1,1-diphosphonic acid disodium salt which, following the procedure described in Example 3, is transformed into N-{[$N^6$, $N^6$-bis(2-chloroethyl)-(DL)-lysinyl-(L)-alanyl]}-4-amino-1-hydroxybutane-1,1-diphosphonic acid dihydrochloride.

EXAMPLE 10

Following the procedure described in Example 1, step c), N'-(tert-butoxycarbonyl)-4-[bis(2-chloroetyl)amino]-(L)-phenylalanine hydroxysuccinimide ester is reacted with 3-(piperazin-1-yl)-1-hydroypropane-1,1-diphosphonic acid to give 3-{4-{N'-(tert-butoxycarbonyl)-4-[bis(2-chloroethyl)amino]-(L)phenylalanyl}-piperazin-1-yl}-1-hydroxypropane-1,1-diphosphonic acid disodium salt.

Following the procedure described in Example 3, this compound is subsequently transformed into 3-{4-{4-[bis(2-chloroethyl)amino]-(L)-phenylalanyl}-piperazin-1-yl}-1-hydroxypropane-1,1-diphosphonic acid monohydrochloride.

$^1$H-NMR (D$_2$O, TMS): $\delta$=2.1 (m, 4H); 3.2 (m, 4H); 3.7 (m, 4H); 3.75 (s, 8H); 3.92 (m, 4H); 4.6 (m, 1H); 7.15 (d, 2H); 7.32 (d, 2H).

EXAMPLE 11

Following the procedure described in Example 10, by reacting the appropriate 1-hydroxy-1,1-diphosphonic acids with N'-(tert-butoxycarbonyl)-4-[bis(2-chloroethyl)amino]-(L)-phenylalanine hydroxysuccinimide ester, the following compounds are obtained:

4-{4-{4-[bis(2-chloroethyl)amino]-(L)-phenylalanyl}-piperazin-1-yl}-1-hydroxybutane-1,1-diphosphonic acid monohydrochloride; $^1$H-NMR (D$_2$O, TMS): $\delta$=2.1 (m, 4H); 3.2 (m, 4H); 3.75 (s, 8H); 3.92 (m, 4H); 4.6 (m, 1H); 7.15 (d, 2H); 7.32 (d, 2H).

N-{4-[bis(2-chloroethyl)amino]-(L)-phenylalanyl}-3-(pirrolidin-2-yl)-1-hydroxypropane-1,1-diphosphonic acid monohydrochloride;

N-{4-[bis(2-chloroethyl)amino]-(L)-phenylalanyl}-3-(piperidin-4-yl)-1-hydroxypropane-1,1-diphosphonic acid monohydrochloride;

N-{4-[bis(2-chloroethyl)amino]-(L)-phenylalanyl}-3-(piperidin-2-yl)-1-hydroxypropane-1,1-diphosphonic acid monohydrochloride;

N-{4-[bis(2-chloroethyl)amino]-(L)-phenylalanyl}-2-(piperidin-2-yl)-1-hydroxyethane-1,1-diphosphonic acid monohydrochloride.

EXAMPLE 12

Following the procedure described in example 1, step C, N-formyl-4-[bis(2-chloroethyl)amino]-(L)-phenylalanie hydroxysuccinimide ester is reacted with 4-(piperazin-1-yl)-1hydroxybutane-1,1-diphosphonic acid to give 4-{4-{N'-formyl-4-[bis(2-chloroethyl)amino]-(L)-phenylalanyl}piperazin-1-yl}-1-hydroxybutane-1,1-diphosphonic acid disodium salt.

$^1$H-NMR (D$_2$O, TMS): δ=1.85 (m, 4H); 2.30 (m, 3H); 2.65 (m, 3H); 2.85 (m, 2H); 3.05 (m, 2H); 3.50 (m, 2H); 3.75 (s, 8H); 4.55 (q, 1H); 6.85 (d, 2H); 7.15 (d, 2H); 8.05 (s, 1H).

EXAMPLE 13

Following the procedure described in example 1, step C, 4-[4-[bis(2-chloroethyl)amino]phenyl]butyric acid hydroxysuccinimide ester is reacted with 4-(piperazin-1-yl)-1-hydroxybutane-1,1-diphosphonic acid to give 4-{4-{[4-[bis(2-chloroethyl)amino]phenyl]butyroyl} piperazin-1-yl}-1-hydroxybutane-1,1-diphosphonic acid disodium salt.

$^1$H-NMR (D$_2$O, TMS): δ=1.85 (m, 6H); 2.10 (t, 2H); 2.30 (m, 2H); 2.55 (t, 2H); 2.70 (m, 2H); 2.85 (m, 2H); 3.05 (m, 2H); 3.48 (m, 2H); 3.80 (s, 8H); 6.85 (d, 2H); 7.20 (d, 2H).

EXAMPLE 14

Acetoxyacetyl chloride (0.324 ml) is dropped into a solution of 4-amino-1-hydroxybutane-1,1-diphosphonic acid (500 mg) in water (5 ml) and 1N NaOH (8 ml), simultaneously adding 1N NaOH (3 ml) to maintain pH between 11 and 12. When the additions are completed, the reaction mixture is stirred at room temperature for 2 hours, then it is diluted with DMF: a precipitate separates which is recovered by centrifugation and purified by redissolution in water (3 ml) and reprecipitated with acetone (30 ml), to give 720 mg of N-(hydroxyacetyl)-4-amino-1-hydroxybutane-1,1-diphosphonic acid trisodium salt; m.p. >260°

$^1$H-NMR: (D$_2$O, TMS): δ=2,0 (m, 4H); 3,05 (t, 2H); 4,9 (s, 2H)

EXAMPLE 15

Following the procedure described in Example 14, by reacting the appropriate 1-hydroxy-1,1-diphosphonic acids with acetoxyacetyl chloride, the trisodium salts of the following compounds are obtained:

N-hydroxyacetyl-5-amino-1-hydroxypentane-1,1-diphosphonic acid;
3-(4-hydroxyacetyl-piperazin-1-yl)-1-hydroxypropane-1,1-diphosphonic acid;
4-(4-hydroxyacetyl-piperazin-1-yl)-1-hydroxybutane-1,1-diphosphonic acid;
3-(N-hydroxyacetyl-pirrolidin-2-yl)-1-hydroxypropane-1,1-diphosphonic acid;
3-(N-hydroxyacetyl-piperidin-4-yl)-1-hydroxypropane-1,1-diphosphonic acid;
3-(N-hydroxyacetyl-piperidin-2-yl)-1hydroxypropane-1,1-diphosphonic acid;
2-(N-hydroxyacetyl-piperidin-2-yl)-1-hydroxyethane-1,1-diphosphonic acid.

EXAMPLE 16

A solution of 4-[4-[bis(2-chloroethyl)amino]phenyl]-butyric acid hydroxysuccinimide ester (240 mg) in DMF (5 ml), prepared according to the procedure described in Example 5, is slowly dropped into a solution of N-hydroxyacetyl-4-amino-1-hydroxybutane-1,1-diphosphonic acid trisodium salt (200 mg) dissolved in water (5 ml) and 1N NaOH (0.5 ml), heated to 40° C. At the end of the addition, heating is continued for 30 minutes, then the reaction mixture is cooled and diluted with DMF (10 ml) to obtain a precipitate which is recovered by centrifugation and purified by redissolution in water and reprecipitation with acetone, to give 350 mg of N-{[4-[4-[bis(2-chloroethyl)amino]phenyl]-butyroyloxy]-acetyl}-4-amino-1-hydroxybutane-1,1-diphosphonic acid (trisodium salt); m.p.>260°

$^1$H-NMR (D$_2$O, TMS): δ=1,85 (m, 4H); 2,25 (t, 2H); 2,55 (t, 2H); 3,2 (t, 2H); 3,75 (s, 8H); 5,05 (s, 2H); 6,85 (d, 2H); 7,2 (d, 2H).

EXAMPLE 17

Following the procedure described in Example 16, by reacting the 1-hydroxy-1,1-diphosphonic acids described in Example 13 with the hydroxysuccinimide esters of 4-[4-[bis(2-chlorethyl)amino]phenyl]butyric acid and of N'-(tert-butoxycarbonyl)-4-[bis(2-chloroethyl)amino]-(L)-phenylalanine, the following optionally deprotected compounds are obtained:

N-{[4-[4-[bis(2-chloroethyl)amino]phenyl]butyroyloxy]-acetyl}-5-amino-1-hydroxypentane-1,1-diphosphonic acid (trisodium salt);
3-{[4-[4-[4-[bis(2-chlorethyl)amino]phenyl]butyroyloxy]acetyl]-piperazin-1-yl}-1-hydroxypropane-1,1-diphosphonic acid (trisodium salt);
4-{[4-[4-[4-[bis(2-chloroethyl)amino]phenyl]-butyroyloxy]acetyl]-piperazin-1-yl}-1-hydroxybutane-1,1-diphosphonic acid (trisodium salt);
N-{[4-[4-[bis(2-chloroethyl)amino]phenyl]butyroyloxy]-acetyl}-3-(pyrrolidin-2-yl)-1-hydroxypropane-1,1-diphosphonic acid (trisodium salt);
N-{[4-[4-[bis(2-chloroethyl)amino]phenyl]butyroyloxy]-acetyl}-3-(piperidin-4-yl)-1-hydroxypropane-1,1-diphosphonic acid (trisodium salt);
N-{[4-[4-[bis(2-chloroethyl)amino]phenyl]butyroyloxy]-acetyl}-3-(piperidin-2-yl)-1-hydroxypropane-1,1-diphosphonic acid (trisodium salt);
N-{[4-[4-[bis(2-chloroethyl)amino]phenyl]butyroyloxy]-acetyl}-2-(piperidin-2-yl)-1-hydroxyethane-1,1-diphosphonic acid (trisodium salt);
N-{[4-[bis(2-chloroethyl)amino]-(L)-phenylalanyloxy]-acetyl}-5-amino-1-hydroxypentane-1,1-diphosphonic acid (monohydrochloride);
3-{{4-[4-[bis(2-chloroethyl)amino]-(L)-phenylalanyloxy]acetyl}-piperazin-1-yl}-1-hydroxypropane-1,1-diphosphonic acid (monohydrochloride);
4-{{4-[4-[bis(2-chloroethyl)amino]-(L)-phenylalanyloxy]acetyl}-piperazin-1-yl}-1-hydroxybutane-1,1-diphosphonic acid (monohydrochloride);
N-{[[4-bis(2-chloroethyl)amino]-(L)-phenylalanyloxy]-acetyl}-3-(pirrolidin-2-yl)-1-hydroxypropane-1,1-diphosphonic acid (monohydrochloride);
N-{[[4-bis(2-chloroethyl)amino]-(L)-phenylalanyloxy]-acetyl}-3-(piperidin-4-yl)-1-hydroxypropane-1,1-diphosphonic acid (monohydrochloride);
N-{[[4-bis(2-chloroethyl)amino]-(L)-phenylalanyloxy]-acetyl}-3-(piperidin-2-yl)-1-hydroxypropane-1,1-diphosphonic acid (monohydrochloride);
N-{[[4-bis(2-chloroethyl)amino]-(L)-phenylalanyloxy]-acetyl}-2-amino-1-hydroxyethane-1,1-diphosphonic acid (monohydrochloride).

We claim:
1. Compounds of formula (I):

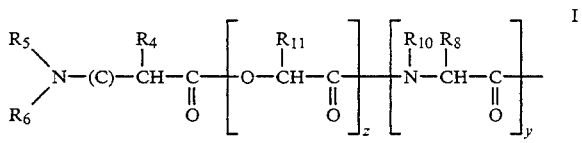

-continued

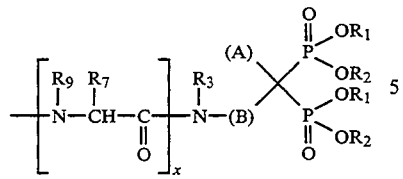

wherein:
R$_1$ and R$_2$, which can be the same or different, are hydrogen or C$_1$-C$_4$ alkyl;
(A) is hydrogen, halogen (chlorine, bromine or iodine), hydroxy, straight or branched C$_1$-C$_{12}$ alkyl;
(B) is a covalent bond, straight or branched C$_1$-C$_8$ alkylene, an alkylene chain containing at least one hetero-atom of formula —[CH(CH$_3$)]$_p$—(CH$_2$)$_{n1}$—X—(CH$_2$)$_n$— or, together with the adjacent nitrogen atom, a group of formula

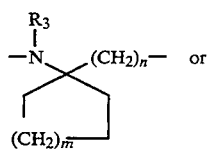 or

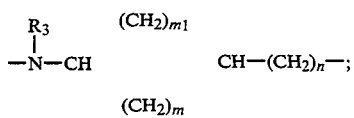

an ortho, meta or para substituted aralkyl of formula

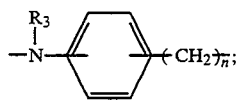

in which;
chain or groups X is O, S, N—CH$_3$;
m is zero or the integer 1 or 2;
m$_1$ is the integer 1, 2, 3 or 4;
n and n$_1$ are an integer from 1 to 5; p is zero or the integer 1; R$_3$ is hydrogen, straight or branched C$_1$-C$_{10}$ alkyl, C$_3$-C$_6$ cycloalkyl, benzyl, phenyl, or p-methoxybenzyl;
(C) is straight or branched C$_1$-C$_5$ alkylene, phenylene, an aralkyl chain of formula

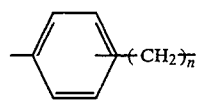

wherein;
n is as defined above;
R$_4$ is selected from hydrogen, straight or branched C$_1$-C$_4$ alkyl, or R$_4$ represents a group

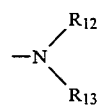

wherein;

R$_{12}$ and R$_{13}$, which are the same or different, are hydrogen, straight or branched C$_1$-C$_6$ alkyl, phenyl, benzyl, para-methoxybenzyl, or one of R$_{12}$ and R$_{13}$ is as defined above and the other one is a group of formula:

wherein;
R$_{14}$ is hydrogen, straight or branched C$_1$-C$_4$ alkyl, phenyl, benzyl, para-methoxybenzyl, straight or branched C$_1$-C$_4$ alkoxyl, halo-C$_1$-C$_4$ alkoxyl;
R$_5$ and R$_6$ are haloethyl or R$_5$ and R$_6$, taken together with the nitrogen atom to which they are linked, are a 1-azyridinyl group of formula

R$_7$, R$_8$, R$_9$ and R$_{10}$, which are the same or different, taken together with the

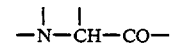

group to which they are linked, are the residue from a D or L amino acid;
R$_{11}$ is hydrogen or straight or branched C$_1$-C$_{12}$ alkyl chain;
x is zero or the integers 1 and 2;
y and z are zero or the integer 1, with the proviso that x, y and z are not at the same time zero, and the pharmaceutically acceptable acids, enantiomers, diastereoisomers and racemates thereof.

2. Compounds according to claim 1, wherein R$_7$, R$_8$, R$_9$ and R$_{10}$, together with the —N—CH—CO— group to which they are linked, form the residue from a D or L amino acid selected from: glycine, sarcosine, alanine, phenylalanine, valine, leucine, isoleucine, methionine, proline.

3. Compounds according to claim 1, wherein (A) is hydroxy.

4. Compounds according to claim 1, wherein (B) is a straight C$_2$-C$_5$ alkylene, a branched alkylene of formula

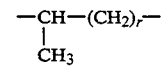

wherein r is from 2 to 5, or one of the chains of formula

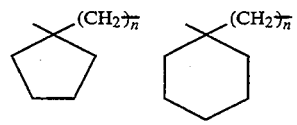

wherein n is from 1 to 4.

5. Compounds according to claim 1, wherein R$_1$ and R$_2$ are hydrogen.

6. Compounds according to claim 1, wherein z is 1 and x and y are zero.

7. Compounds according to claim 1, wherein x and y are different from zero and z is zero.

8. Compounds according to claim 1, wherein x is 1 and y and z are zero.

9. Pharmaceutical compositions containing as the active ingredient a compound according to claim 1, in admixture with a suitable carrier.

10. A method of treating a patient suffering from a tumor, comprising administering to a patient in need of such treatment an antitumor effective amount of at least one of the compounds according to claim 1.

* * * * *